(12) United States Patent
Berlatzky et al.

(10) Patent No.: US 9,354,212 B2
(45) Date of Patent: May 31, 2016

(54) INSPECTION HAVING A SEGMENTED PUPIL

(71) Applicant: APPLIED MATERIALS ISRAEL, LTD., Rehovot (IL)

(72) Inventors: Yoav Berlatzky, DN Lachish South (IL); Amir Shoham, Haifa (IL); Ido Dolev, Rehovot (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 153 days.

(21) Appl. No.: 14/149,645

(22) Filed: Jan. 7, 2014

(65) Prior Publication Data
US 2015/0193926 A1 Jul. 9, 2015

(51) Int. Cl.
*G06K 9/00* (2006.01)
*G01N 33/00* (2006.01)
*G01N 21/88* (2006.01)

(52) U.S. Cl.
CPC ............ *G01N 33/00* (2013.01); *G01N 21/8806* (2013.01); *G01N 2021/8822* (2013.01); *G01N 2033/0095* (2013.01)

(58) Field of Classification Search
None
See application file for complete search history.

(56) References Cited

U.S. PATENT DOCUMENTS

| | | | | |
|---|---|---|---|---|
| 5,185,810 A * | 2/1993 | Freischlad | ......... | G01B 11/2441 356/513 |
| 5,303,709 A * | 4/1994 | Dreher | ................. | A61B 3/1225 351/206 |
| 5,548,444 A * | 8/1996 | McLaughlin | .......... | G02B 27/09 359/629 |
| 6,630,827 B1 * | 10/2003 | Miyoshi | ............... | G01R 33/565 342/307 |
| 8,164,040 B2 * | 4/2012 | Fan | .................... | G02B 27/0081 250/201.1 |
| 8,456,641 B1 * | 6/2013 | Levinski | ................ | G01N 21/55 356/445 |
| 2010/0141925 A1 * | 6/2010 | Cao | ......................... | G03F 7/705 355/77 |
| 2012/0194721 A1 * | 8/2012 | Sakaida | ............. | H04N 5/23212 348/302 |
| 2013/0301024 A1 * | 11/2013 | Conradi | .............. | G03F 7/70483 355/67 |

* cited by examiner

*Primary Examiner* — Jayesh A Patel
(74) *Attorney, Agent, or Firm* — Kilpatrick Townsend & Stockton LLP

(57) ABSTRACT

A method and an apparatus that may include optics that is arranged to illuminate a surface of a sample with radiation and to collect reflected radiation from the surface of the sample; wherein the optics includes a pupil that has multiple pupil segments that correspond to different angular regions of collection or illumination; and a detection module arranged to receive the reflected radiation and generate, for each pupil segment, pupil segment detection signals.

22 Claims, 20 Drawing Sheets

1010

1020

INSPECTION HAVING A SEGMENTED PUPIL

BACKGROUND OF THE INVENTION

Semiconductor wafers are manufactured by highly complex manufacturing processes. These manufacturing processes are monitored by inspection tools that are aimed to find various types of defects by applying defect detection algorithms.

There is a growing need to provide faster and more reliable defect detection systems. U.S. Pat. No. 8,456,641 discloses an Optical system.

SUMMARY

According to an embodiment of the invention a method may be provided and may include: (i) receiving pupil segment detection signals related to multiple pupil segments; and processing (ii), by an image processor, pupil segment detection signals from at least two different pupil segments to provide shape information about the surface of the sample.

According to an embodiment of the invention the pupil segment detection signals may be generated by a process that may include: (a) illuminating, by optics, a surface of a sample with radiation; (b) collecting, by the optics, reflected radiation from the surface of the sample; wherein the optics comprises an pupil having the multiple pupil segments; wherein different pupil segments correspond to different angular regions of collection or illumination; (c) receiving, by a detection module, the reflected radiation; and generating (d), by the detection module, for each pupil segment pupil segment detection signals. The radiation can be visible, light, ultra violet (UV), deep UV or extreme UV radiation.

The method may include generating the pupil segment detection signals.

The method may include generating the pupil segment detection signals by illuminating, by optics, a surface of a sample with radiation; collecting, by the optics, reflected radiation from the surface of the sample; wherein the optics comprise an pupil that comprises multiple pupil segments that correspond to different angular regions of collection or illumination; receiving, by a detection module, the reflected radiation; and generating, by the detection module, for each pupil segment pupil segment detection signals.

The method may include processing, by an image processor, pupil segment detection signals from at least two different pupil segments to provide shape information about the surface of the sample.

The method may include processing pupil segment detection signals from at least two different pupil segments to provide amplitude and phase information relating to the surface of the sample.

The method may include at least one out of (i) summing pupil segment detection signals from at least two different pupil segments to provide the amplitude information; and (ii) subtracting pupil segment detection signals from at least two different pupil segments to provide the phase information.

Additional embodiments of the invention include an apparatus arranged to execute any or all of the methods described above, including any stages—and any combinations of same. For example, the apparatus may include (i) optics that are arranged to illuminate a surface of a sample with radiation and to collect reflected radiation from the surface of the sample; wherein the optics comprise an pupil that comprises multiple pupil segments that correspond to different angular regions of collection or illumination; and (ii) a detection module arranged to receive the reflected radiation and generate, for each pupil segment, pupil segment detection signals.

The apparatus may include an image processor arranged to process pupil segment detection signals from at least two different pupil segments to provide shape information of the surface of the sample.

The apparatus may include an image processor arranged to process pupil segment detection signals from at least two different pupil segments to provide amplitude and phase information relating to the surface of the sample.

The apparatus may include an image processor arranged to sum pupil segment detection signals from at least two different pupil segments to provide the amplitude information and, additionally or alternatively, to subtract pupil segment detection signals from at least two different pupil segments to provide the phase information.

The optics may be arranged to scan the surface of the sample with a beam of radiation and wherein the multiple pupil segments correspond to different angular regions of collection.

The optics may apply area illumination and wherein the multiple pupil segments correspond to different angular regions of illumination.

The detection module may be arranged to receive the reflected radiation from all of the pupil segments concurrently.

The detection module may be arranged to receive the reflected radiation from a single pupil segment at a time.

The optics may be arranged to illuminate one pupil segment at a time.

Further embodiments of the invention include a computer readable medium that is non-transitory and may store instructions for performing the above-described methods and any steps thereof, including any combinations of same. For example, the computer readable medium may store instructions that cause a computer to: receive pupil segment pupil segment detection signals related to multiple pupil segments; and process, by an image processor, pupil segment detection signals from at least two different pupil segments to provide shape information about the surface of the sample; wherein the pupil segment detection signals are generated by: illuminating, by optics, a surface of a sample with radiation; collecting, by the optics, reflected radiation from the surface of the sample; wherein the optics comprises an pupil having the multiple pupil segments; wherein different pupil segments correspond to different angular regions of collection or illumination; receiving, by a detection module, the reflected radiation; and generating, by the detection module, for each pupil segment pupil segment detection signals.

The non-transitory computer readable medium may store instructions that cause the computer to process pupil segment detection signals from at least two different pupil segments to provide amplitude and phase information relating to the surface of the sample.

The non-transitory computer readable medium may store instructions that cause the computer to sum pupil segment detection signals from at least two different pupil segments to provide the amplitude information and to subtract pupil segment detection signals from at least two different pupil segments to provide the phase information.

According to an embodiment of the invention there may be provided an apparatus that may include optics that has an optical axis that are arranged to illuminate a surface of a sample with radiation and to collect reflected radiation from the surface of the sample; wherein the optics comprise a pupil that comprises an off-axis pupil segment that correspond to a certain angular region of collection or illumination; wherein an optical axis of the off-axis pupil differs from an optical axis of the optics; and a detection module arranged to receive the reflected radiation and generate, for the off-axis pupil segment, pupil segment detection signals.

The may include an image processor arranged to process pupil segment detection signals from the off-axis pupil segment to provide shape information of the surface of the sample.

According to an embodiment of the invention a method may be provided and may include: (i) receiving pupil segment pupil segment detection signals related to an off-axis pupil segment; and processing (ii), by an image processor, pupil segment detection signals from the off-axis pupil segment to provide shape information about the surface of the sample.

According to an embodiment of the invention a method may be provided and may include: illuminating, by optics, a surface of a sample with radiation; collecting, by the optics, reflected radiation from the surface of the sample; wherein the optics comprise an off-axis pupil that corresponds to a certain angular region of collection or illumination; receiving, by a detection module, the reflected radiation; and generating, by the detection module, for the off-axis pupil segment pupil segment detection signals.

Further embodiments of the invention include a computer readable medium that is non-transitory and may store instructions for performing the above-described methods and any steps thereof, including any combinations of same. For example, the computer readable medium may store instructions that cause a computer to: illuminating, by optics, a surface of a sample with radiation; collecting, by the optics, reflected radiation from the surface of the sample; wherein the optics comprise an off-axis pupil that corresponds to a certain angular region of collection or illumination; receiving, by a detection module, the reflected radiation; and generating, by the detection module, for the off-axis pupil segment pupil segment detection signals.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
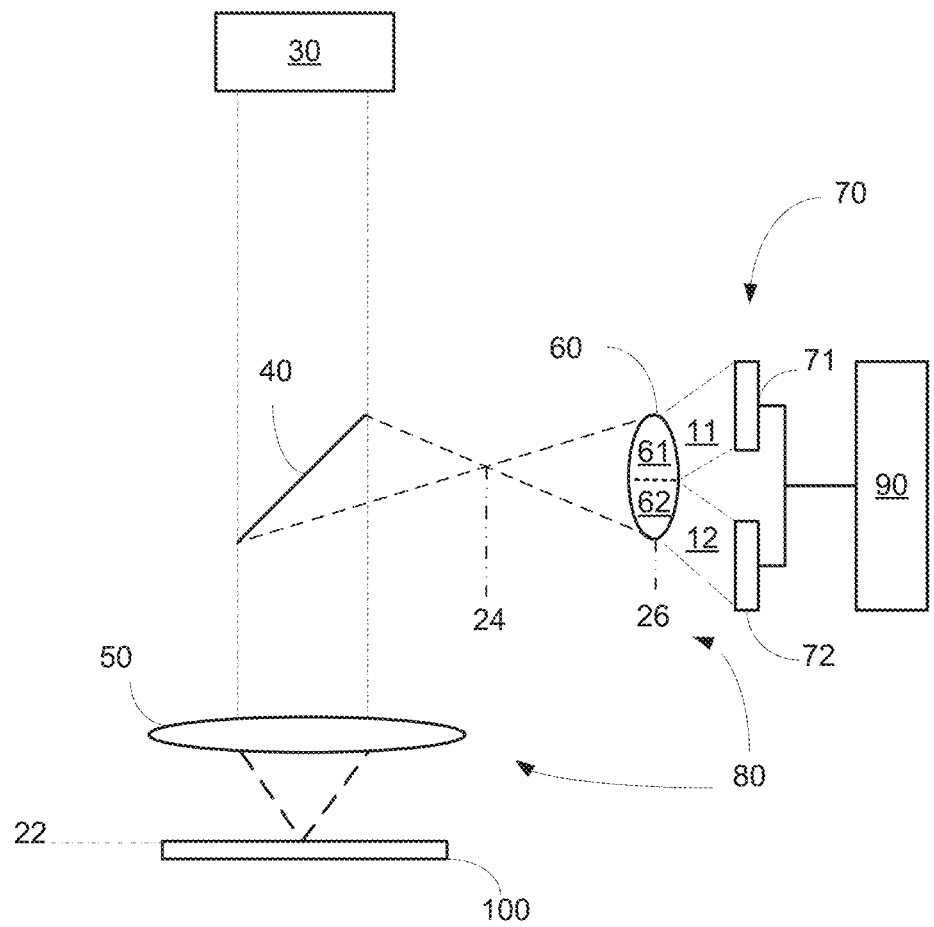
FIG. 1 illustrates a sample and an apparatus according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that can be executed by the system and should be applied mutatis mutandis to a non-transitory computer readable medium that stores instructions that can be executed by the system.

Any reference in the specification to a non-transitory computer readable medium should be applied mutatis mutandis to a system capable of executing the instructions stored in the non-transitory computer readable medium and should be applied mutatis mutandis to method that can be executed by a computer that reads the instructions stored in the non-transitory computer readable medium.

According to an embodiment of the invention there may be provided an apparatus in which an optical imaging system's pupil is segmented. The pupil can be positioned in the collection path of a scanning system, such as a flying spot system, a traveling lens system and the like. The pupil can be positioned in the illumination path of an area microscope that illuminates one area after the other.

The pupil can be divided into segments (halves, thirds, quadrants, etc.) to provide pupil segments that do not overlap (either completely non-overlap or partially overlap). The pupil segments can be of equal shape and size but may differ from each other by shape and additionally or alternatively by size.

The pupil is located at a plane (pupil plane) in which location corresponds to collection or illumination angle. Different pupil segments are positioned in different locations and each detects light from different angular range.

Figure 12:
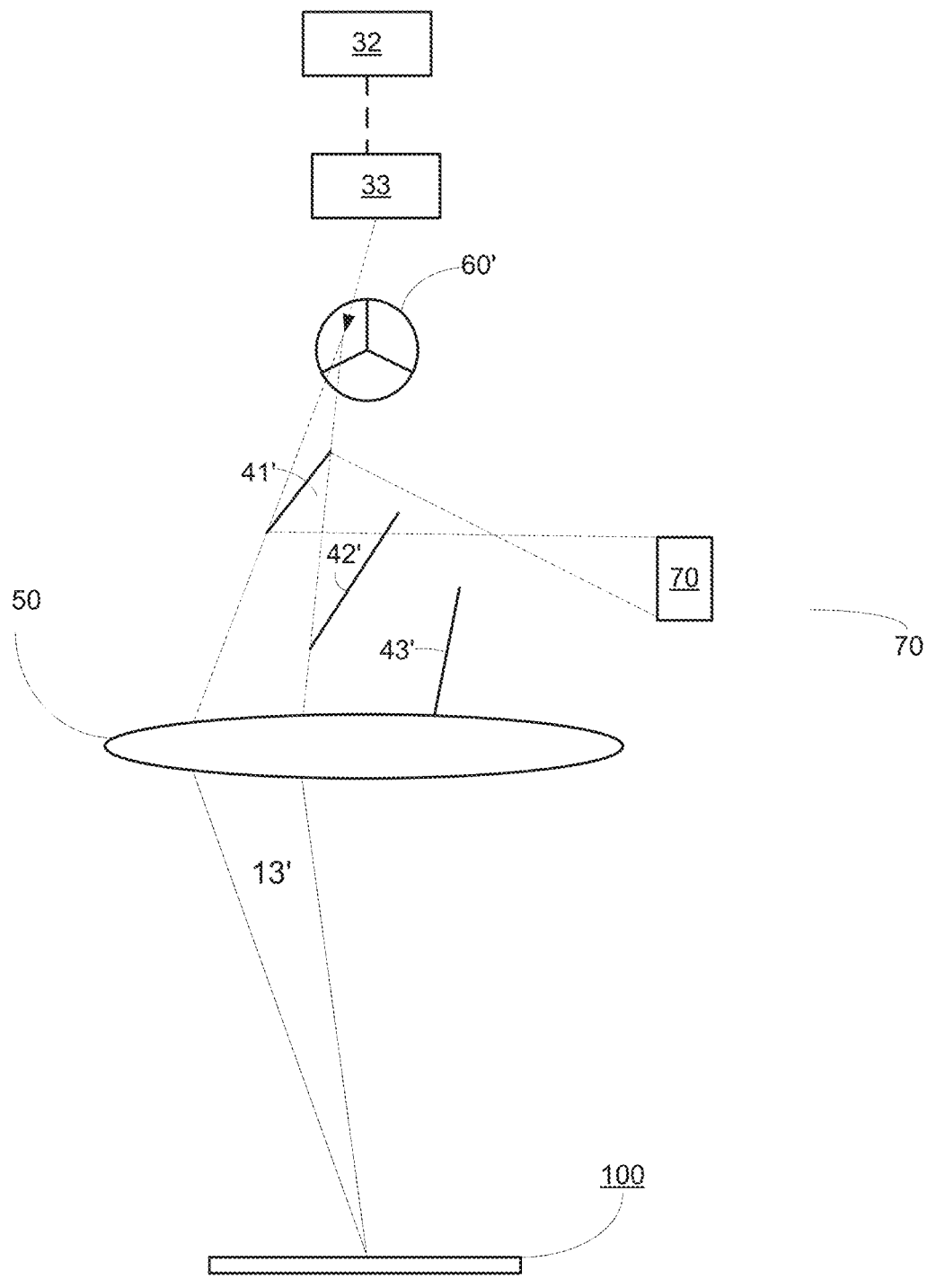
FIGS. 12-14 illustrate a sample and an apparatus at different points in time according to an embodiment of the invention.
Figure 13:
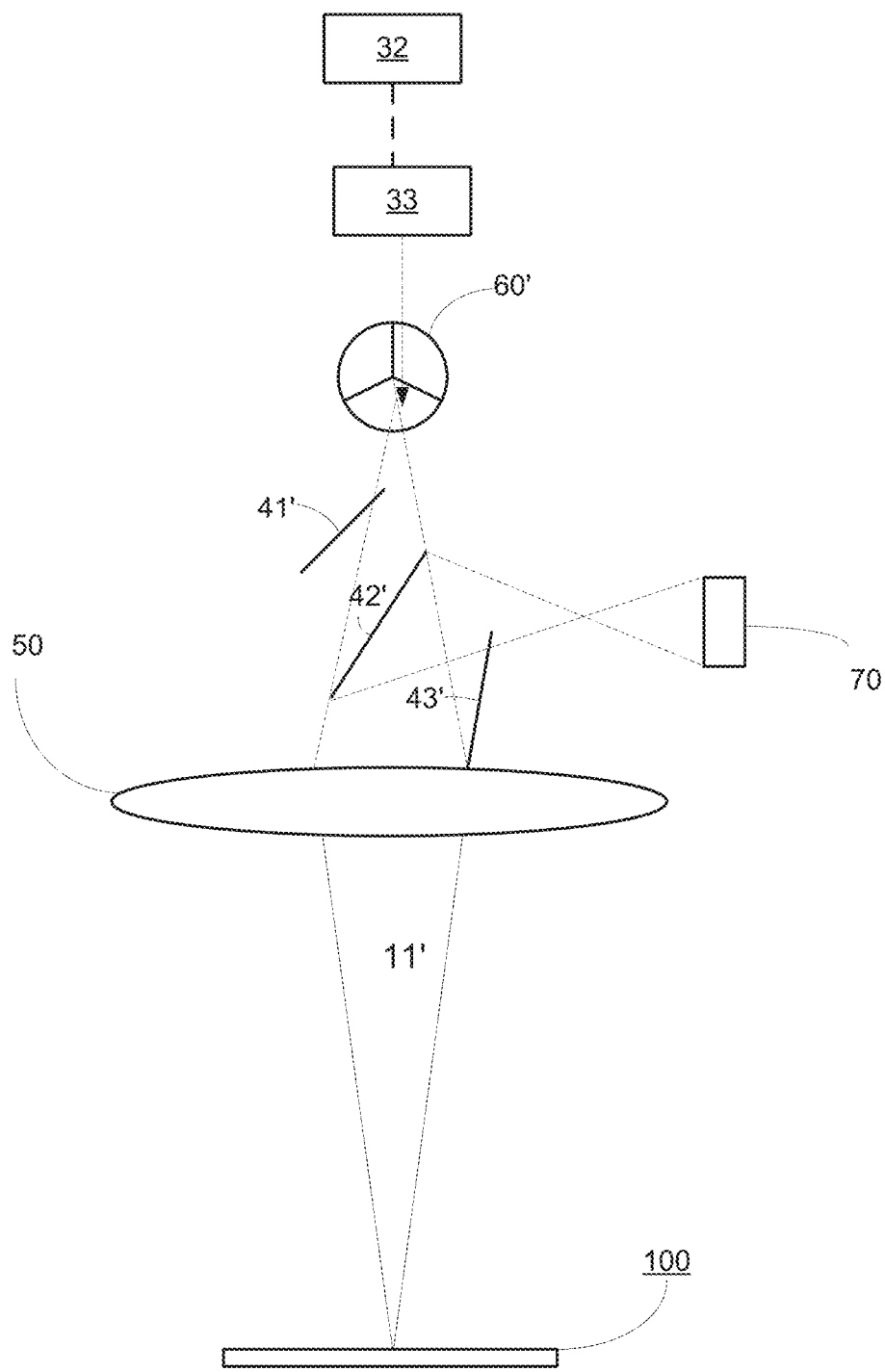
Figure 14:
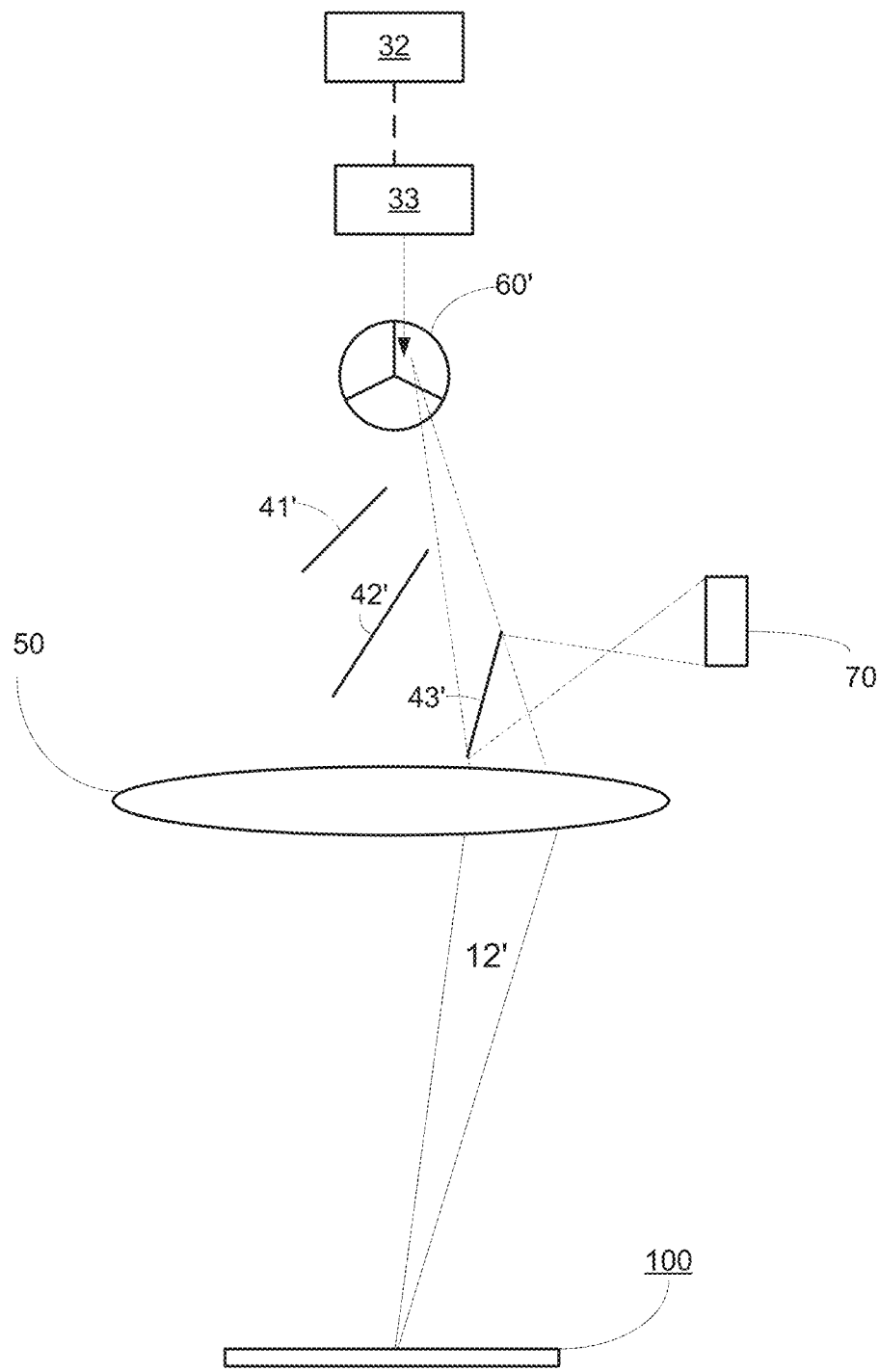

The apparatus may be arranged to generate an image for each pupil segment. In a flying spot system this may be done simultaneously—images belonging to different segments can be collected concurrently. In an area microscope images of different pupil segments may be grabbed for each segment individually—either concurrently or in a sequential manner. This may be done e.g. by using a pulsed light source that illuminates each individual pupil segment in turn, so that individual segment images are grabbed, one for each pulse. FIGS. 12-14 illustrate a system 10" at three different points of time—corresponding to the sequential illumination of three segments of the pupil.

Figure 11:
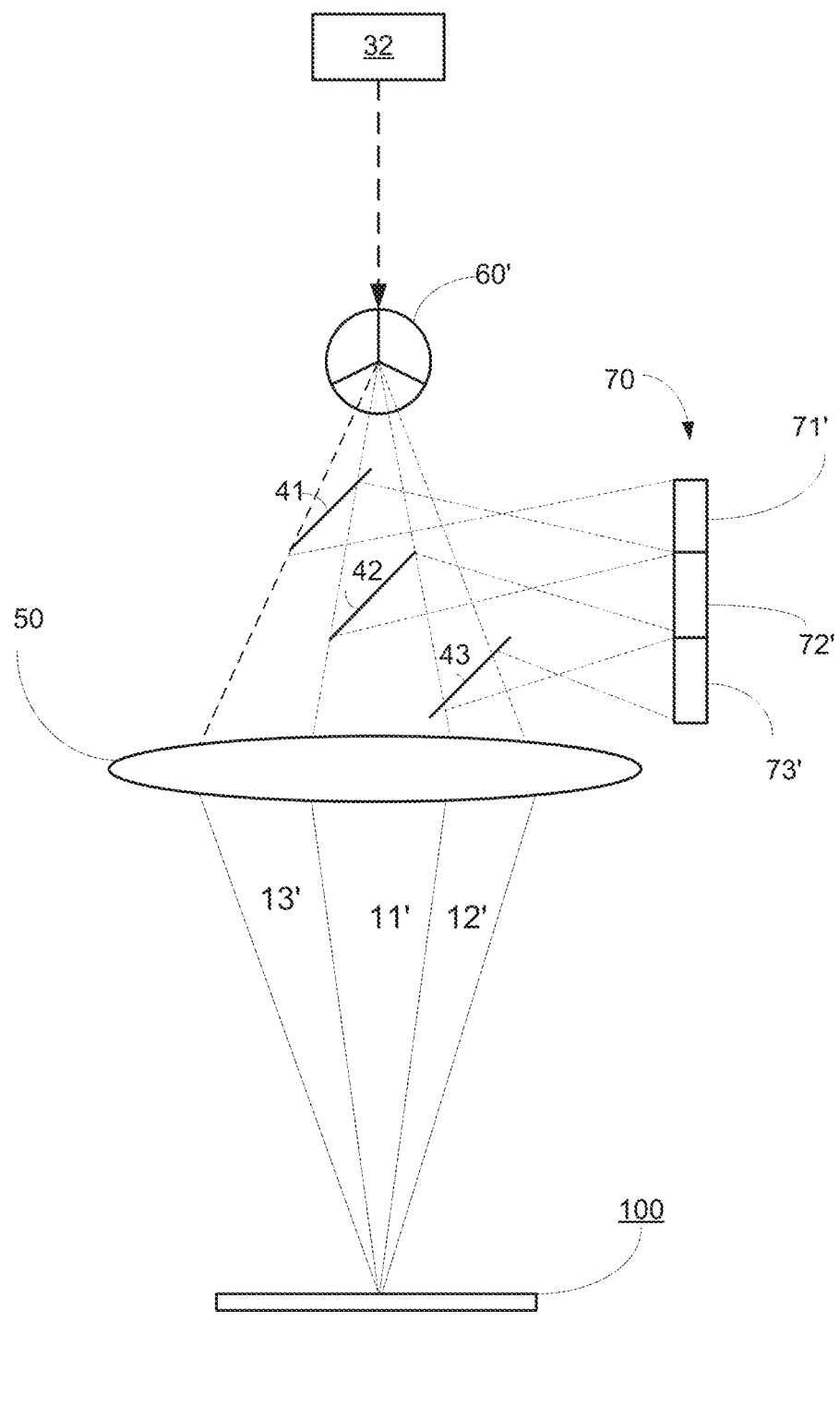
FIG. 11 illustrates a sample and an apparatus according to an embodiment of the invention.

Another option is to divide the field of view so that each portion of the field of view is illuminated by a different segment. FIG. 11 illustrates a system 10' in which three different pupil segment are illuminated concurrently and the images obtained from this illuminations are collected (concurrently) by three different portions of a sensor. In a scanning tool, according to an embodiment of the invention, the scan plan is adjusted so that eventually each area in the inspected target is covered by all segments.

Once an image is obtained for each pupil segment, image processing is used to recover phase and amplitude information. In one implementation with only two pupil segments (each one covering one half), there are provided two images, I1 and I2 corresponding to each pupil segment.

A sum image that is obtained by combining I1+I2 may provide amplitude information, while a difference image obtained by subtracting one image from the other (I1−I2) may provide a gradient of the phase information. Integration of the difference image may provide a phase/height map.

When using N segments, full phase information can be recovered using various techniques. The sum I1+ . . . +IN describes the amplitude information. Various combinations of I1, . . . , IN may be used to calculate gradients. These gradients may then be used to reconstruct the height/phase map.

The apparatus may fully recover the phase information or only partially recover the phase information using the above image processing techniques.

In many cases the different images from the segments provide enough attributes for classification of the defect types.

According to an embodiment of the invention one or more images from a single pupil segment that is off-axis (light that exits the pupil segment propagates along a path that differ from the optical axis of the imaging and/or collection path) can provide sufficient information for classifying defects.

Figure 2:
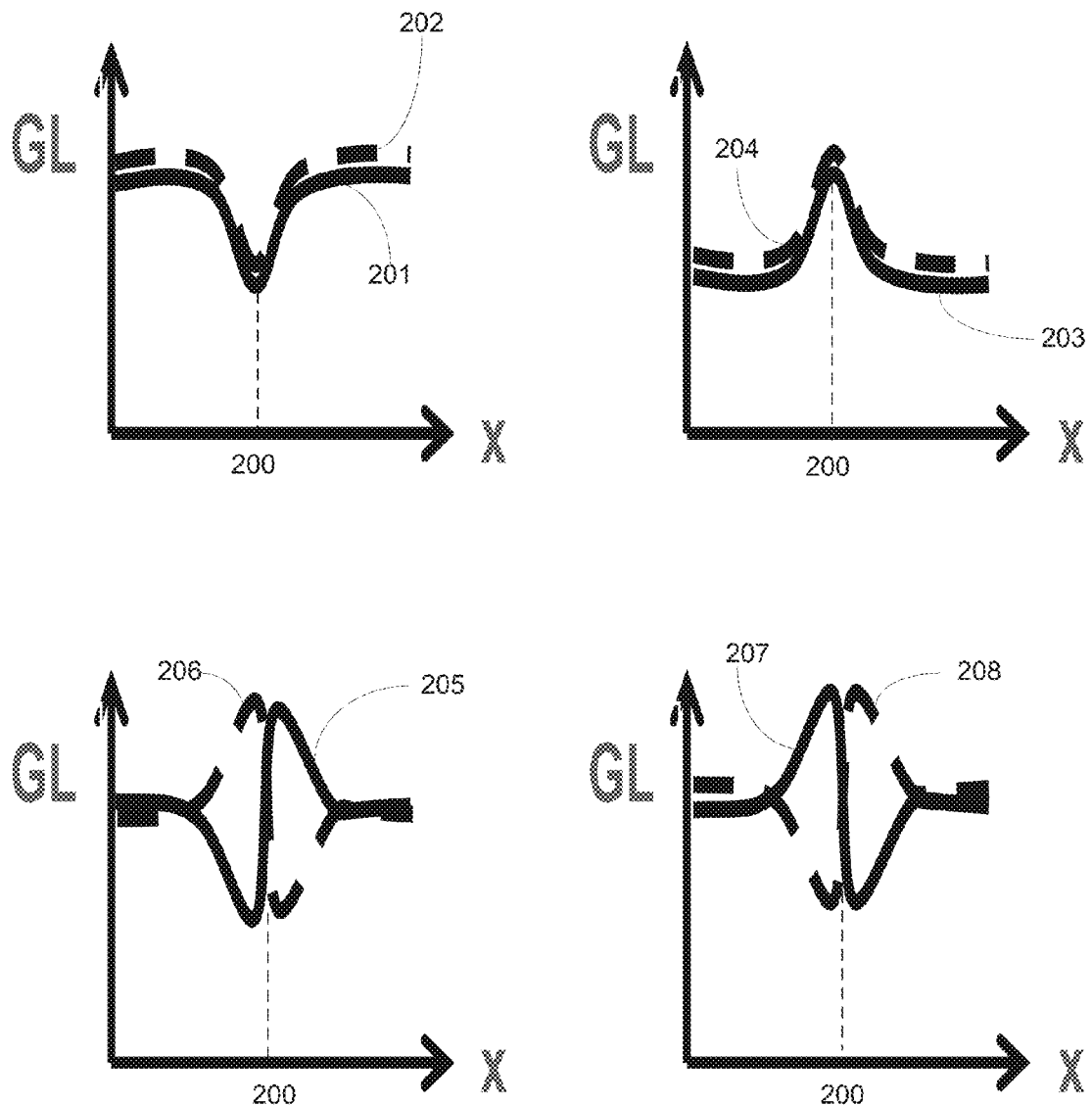
FIG. 2 illustrates pupil segment detections signals obtained when illuminating defects of different characteristics according to various embodiments of the invention.
Figure 3:
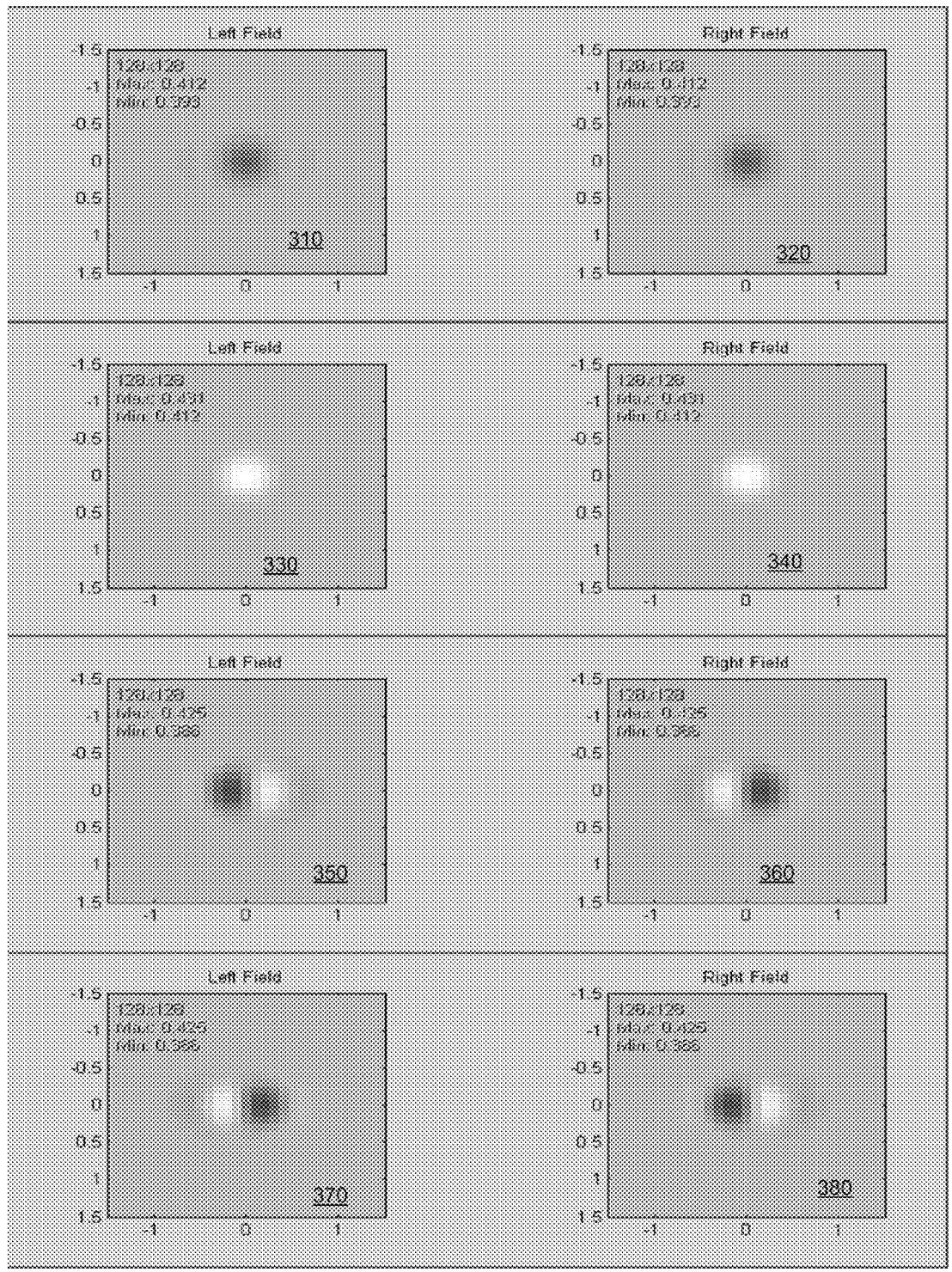
FIG. 3 illustrates simulation results of various pupil segment detections signals according to various embodiments of the invention.

According to an embodiment of the invention employing a single off-axis pupil segment, one may obtain enough optical information for defect detection and/or classification. As shown in FIGS. 2 and 3, by using the image from only one detector one obtains a distinct signature for the different types of defect—e.g. absorbing, reflective, positive phase and negative phase. This results in a greatly simplified optical setup that generates enough useful new information in a single image regarding the defect's phase and amplitude as compared to conventional microscopy techniques that are optimized to detect either amplitude (conventional bright-field) or phase (phase contrast).

For example, in a two pupil segment case described above, an absorbing amplitude defect will have I1 and I2 values that have negative contrast. A reflective amplitude defect will have I1 and I2 with positive contrast. Phase defects will have signatures that have alternating positive/negative or negative/positive contrast. The same carries on for more segments.

Figure 17:
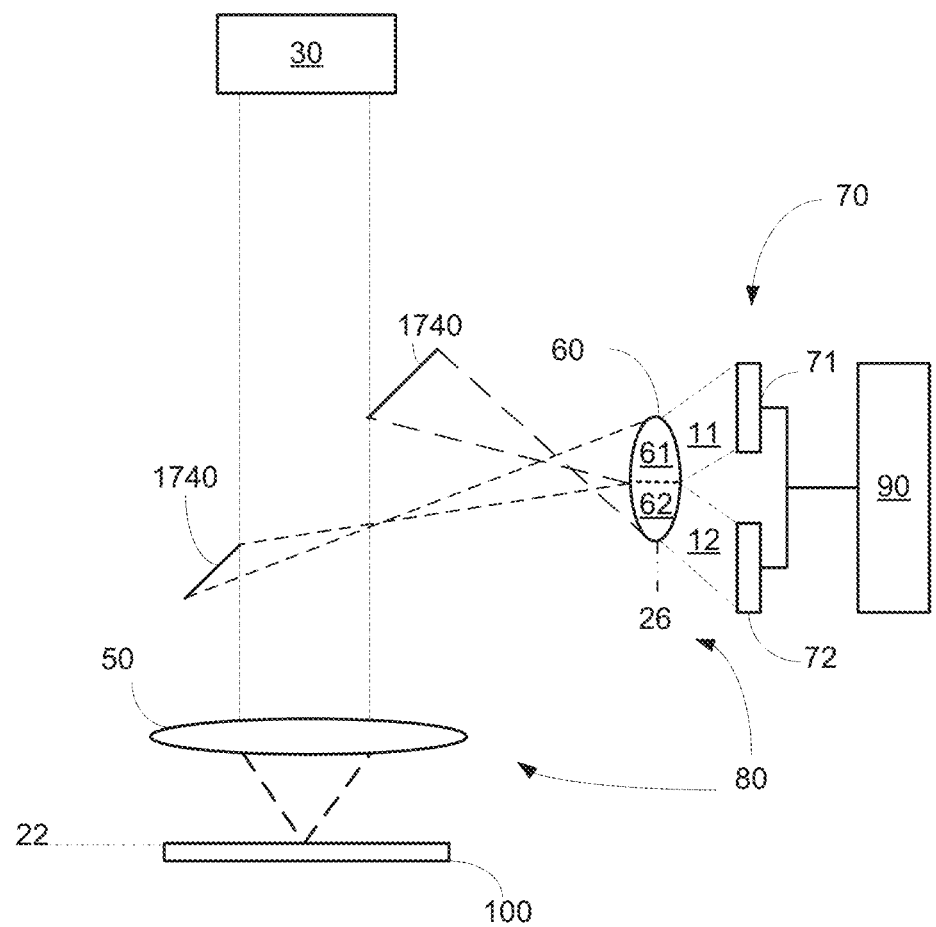
FIG. 17 illustrates a sample and an apparatus according to an embodiment of the invention.
Figure 20:
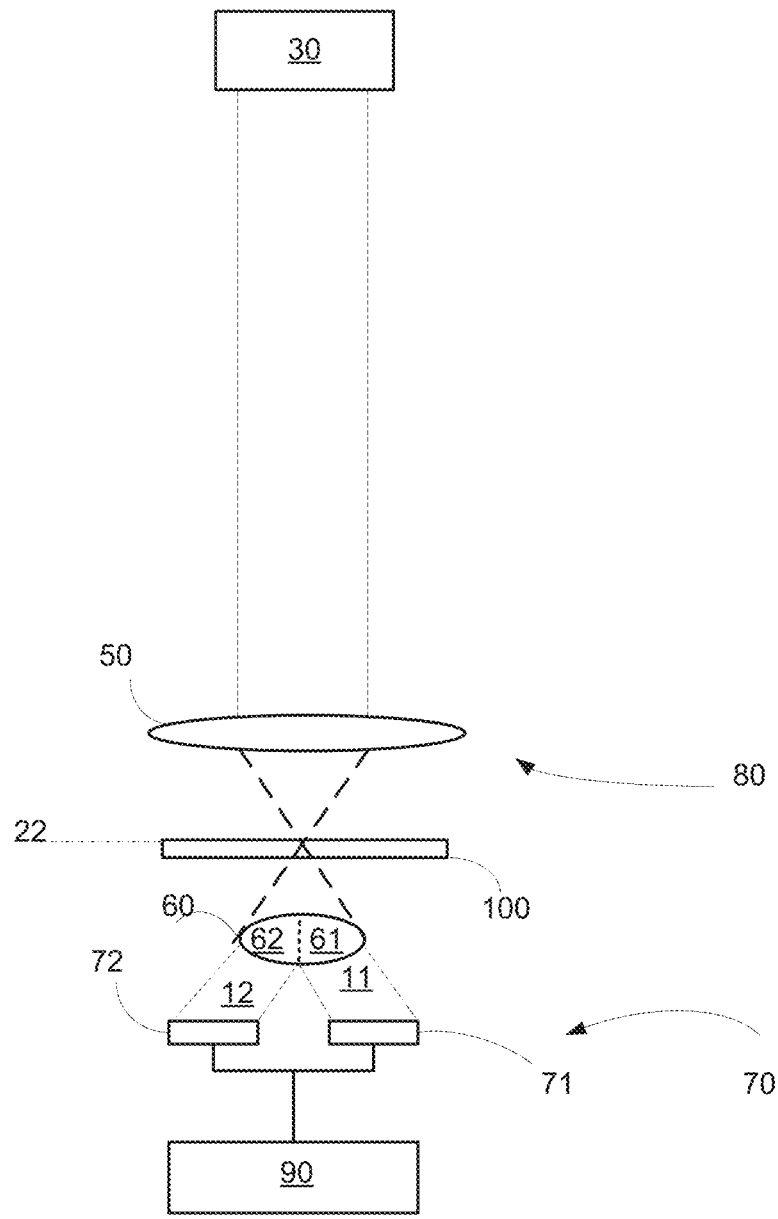
FIG. 20 illustrates a sample and an apparatus according to an embodiment of the invention.

Some of the following examples refer to bright-field optics and to detection of reflected radiation. These may be regarded as non-limiting examples of embodiments of the invention. For example other embodiments may include dark-field or gray field (both are types of off-axis) optics, detection of transmitted radiation, detection of scattered radiation and the like. For example, FIG. 17 illustrates a dark field system and FIG. 20 illustrates a transmissive system while FIGS. 1 and 11-14 illustrate bright-field systems. Any reference to a bright-field system should be applied mutatis mutandis to an off-axis system. Any reference to reflected radiation should be applied mutatis mutandis to scattered radiation and/or transmissive radiation.

FIG. 1 illustrates apparatus 10 and sample 100 according to an embodiment of the invention.

FIG. 1 also illustrates the plane 22 of the object (coincides with the surface of the object 100 that is being illuminated), the image plane 24 and the pupil plane 26.

Apparatus 10 includes bright-field optics 80 and detection module 70. Apparatus 10 may also include an image processor 90 although, additionally or alternatively, the image processor can belong to another apparatus—such as a standalone computer, a server, a remote evaluation or defect detection system and the like.

The bright-field optics 80 are arranged to illuminate a surface of sample 100 with radiation and to collect reflected radiation from the surface of the sample 100.

The bright-field optics 80 may include radiation source 30, beam splitter 40, lens 50, pupil 60 (located at the pupil plane 26) that includes multiple pupil segments (such as 61 and 62) that correspond to different angular regions of collection or illumination (angular ranges 11 and 12 are illustrated). FIG. 1 illustrates a bright-field beam splitter 40 that directs reflected radiation towards pupil 60.

The pupil can include prisms, diffraction gratings or other optical components arranged to direct radiation from or to different pupil segments to different locations.

The detection module 70 can include one or more detectors such as detectors 71 and 72. A detector can be allocated per pupil segment but this is not necessarily so.

The detection module 70 may be arranged to receive the reflected radiation and generate, for each pupil segment, pupil segment detection signals. For example, in FIG. 1 the pupil 60 has two segments 61 and 62. Radiation from first pupil segment 61 is directed onto first detector 71 and radiation from second pupil segment 62 is directed onto second detector 72.

First detector 71 may generate, in response to the radiation from the first segment 61, first pupil segment detection signals.

Second detector 72 may generate, in response to the radiation from the second segment 62, second pupil segment detection signals.

Figure 7:
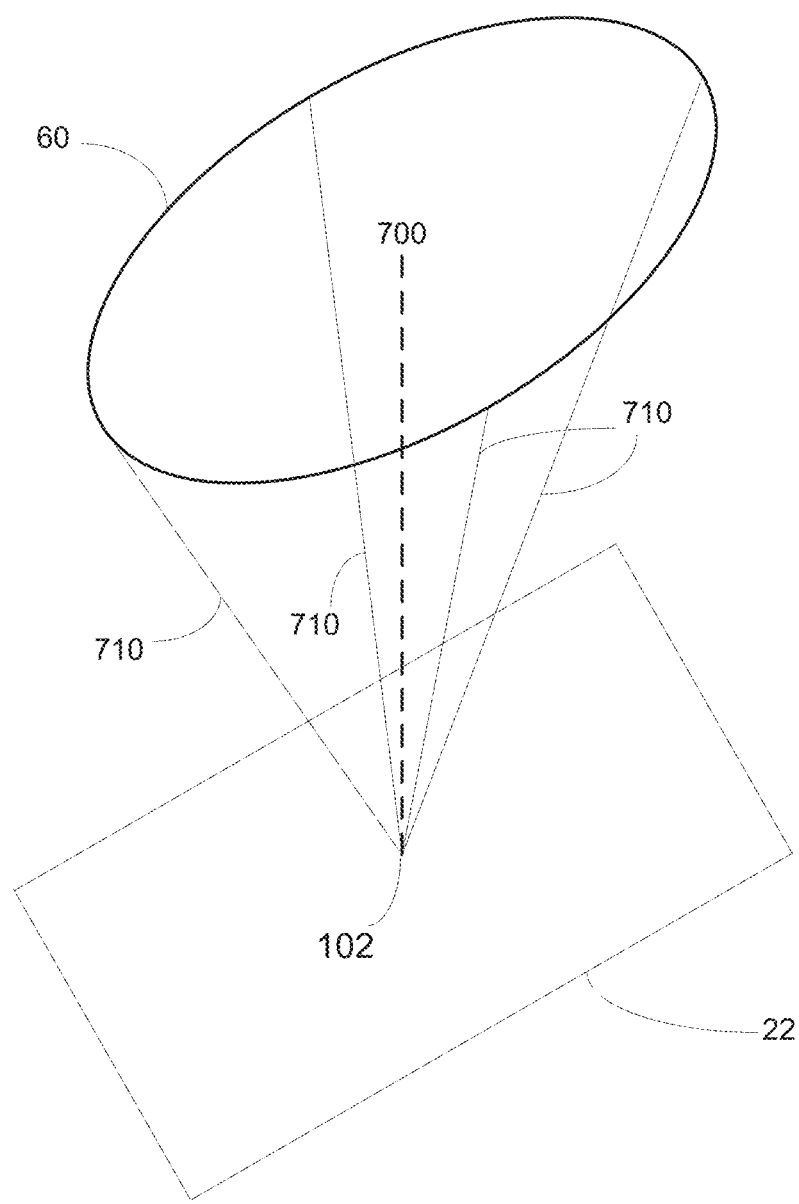
FIGS. 7-9 illustrate various angular ranges and various pupil segments according to various embodiments of the invention.
Figure 8:
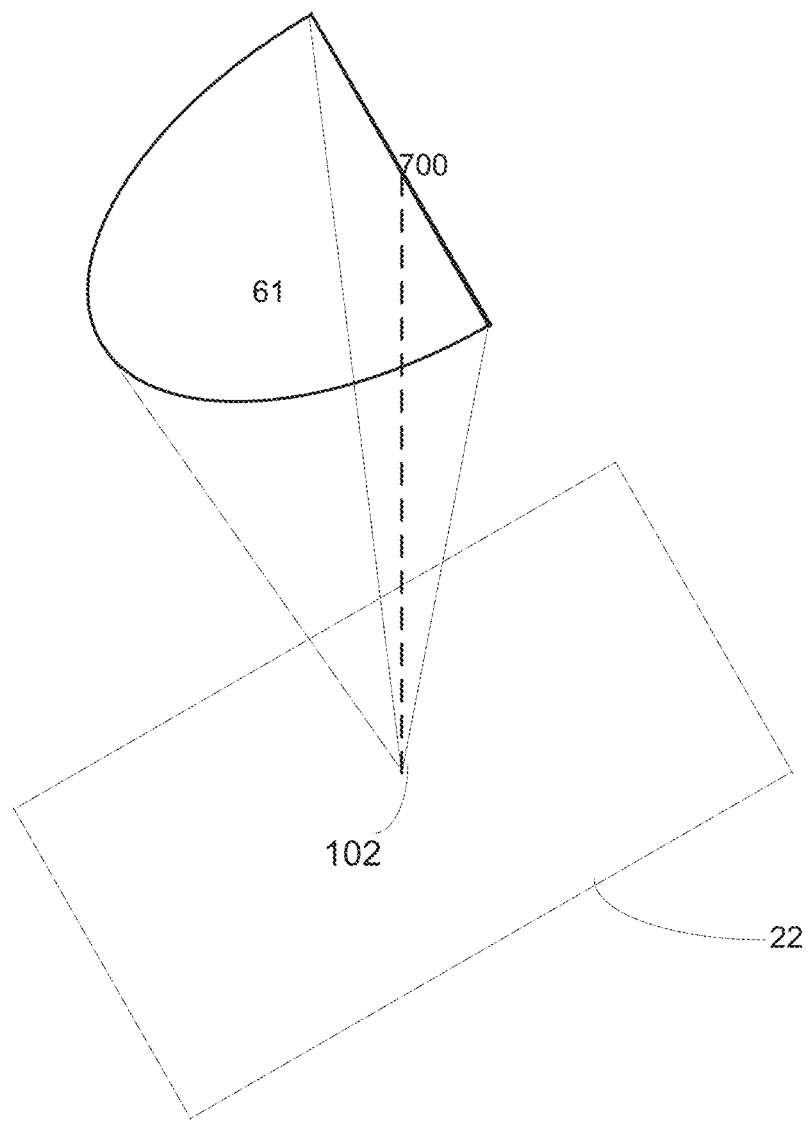
Figure 9:
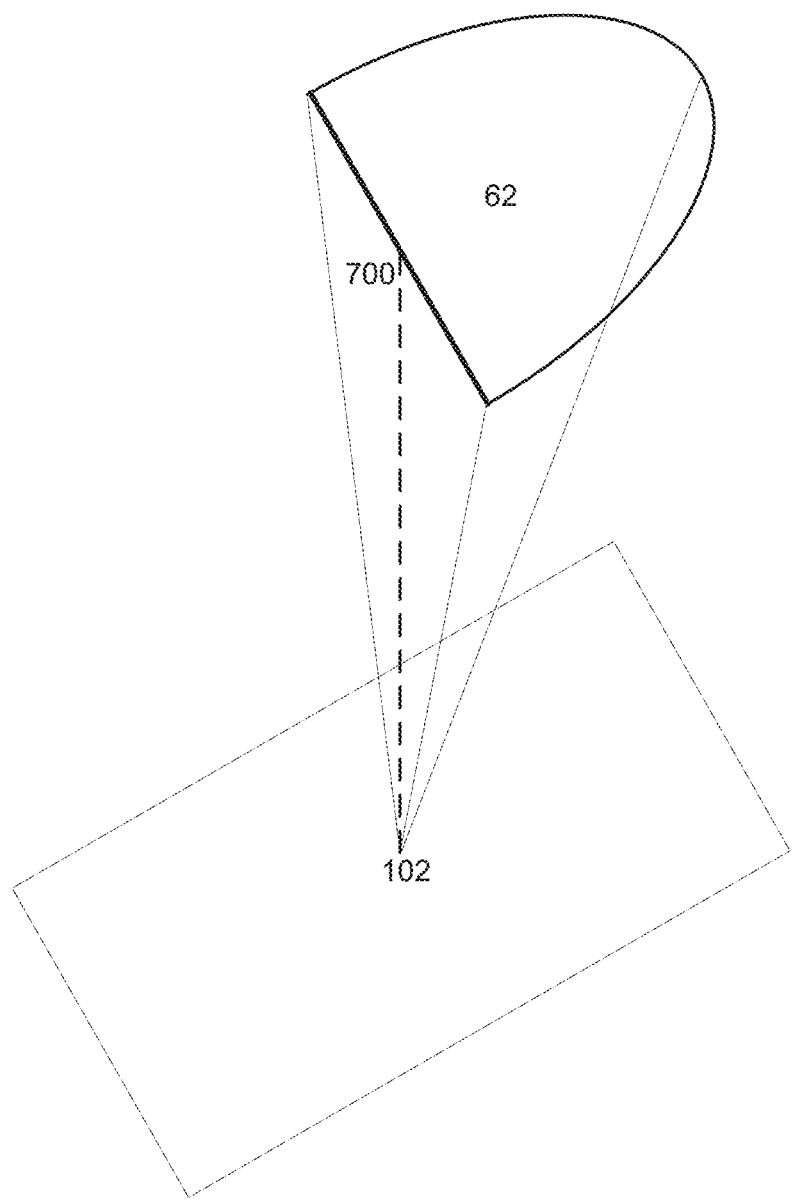

Relationships between location at the pupil and angular ranges are illustrated in FIGS. 7-9. FIGS. 7-9 illustrates angular ranges associate with the entire pupil, a first pupil segment and a second pupil segment according to an embodiment of the invention.

FIG. 7 illustrates a pupil 60, a plane 22 of the object (100), a normal 700 to the plane 22 and a cone of light (delimited by lines 710) collected by the entire pupil 60. FIG. 8 illustrate a half cone of light collected by a first pupil segment 61 and FIG. 9 illustrates another half cone of light collected by the second pupil segment 62.

According to an embodiment of the invention registration between images obtained by (a) a first iteration that involves illuminating the first pupil segment, (b) a second iteration that involves illuminating the second pupil segment, and (c) a third iteration that involves illuminating first and second pupil segments, can be obtained by comparing the image obtained during the third iteration to a combination of images obtained during the first and second iterations. Equilibrium can be obtained once the first and second iteration images are aligned.

Figure 18:
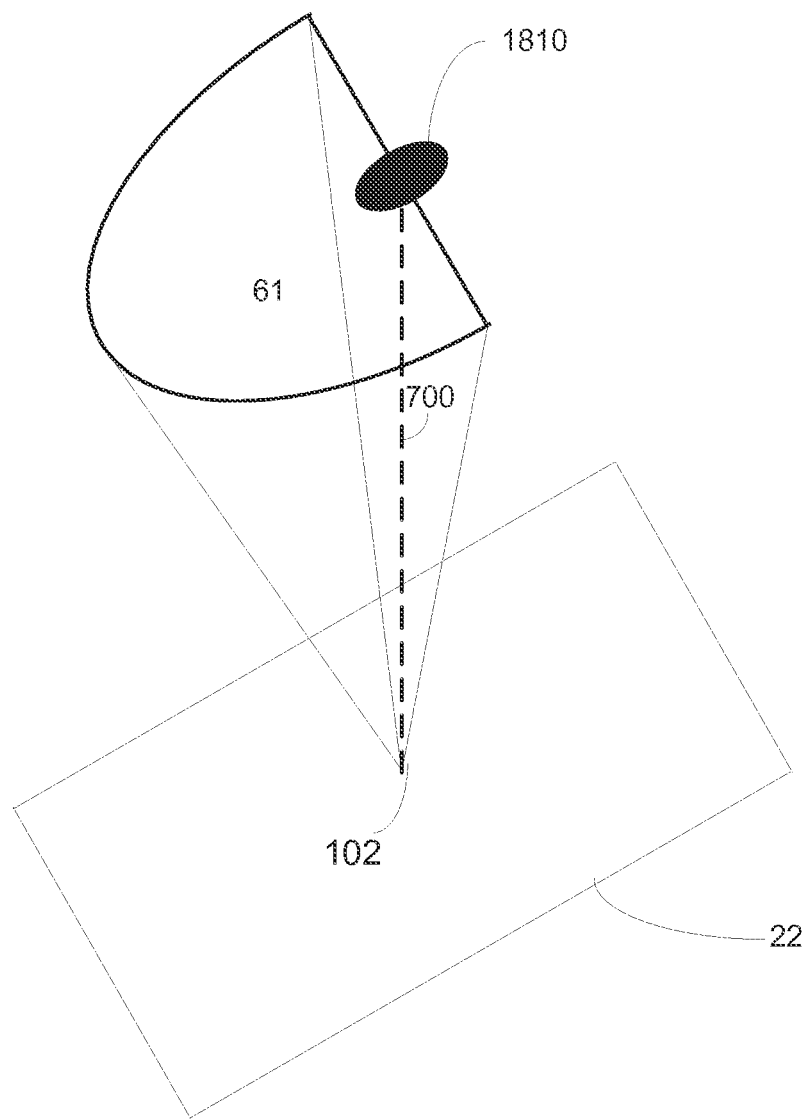
FIGS. 18-19 illustrate various angular ranges and various pupil segments according to various embodiments of the invention.
Figure 19:
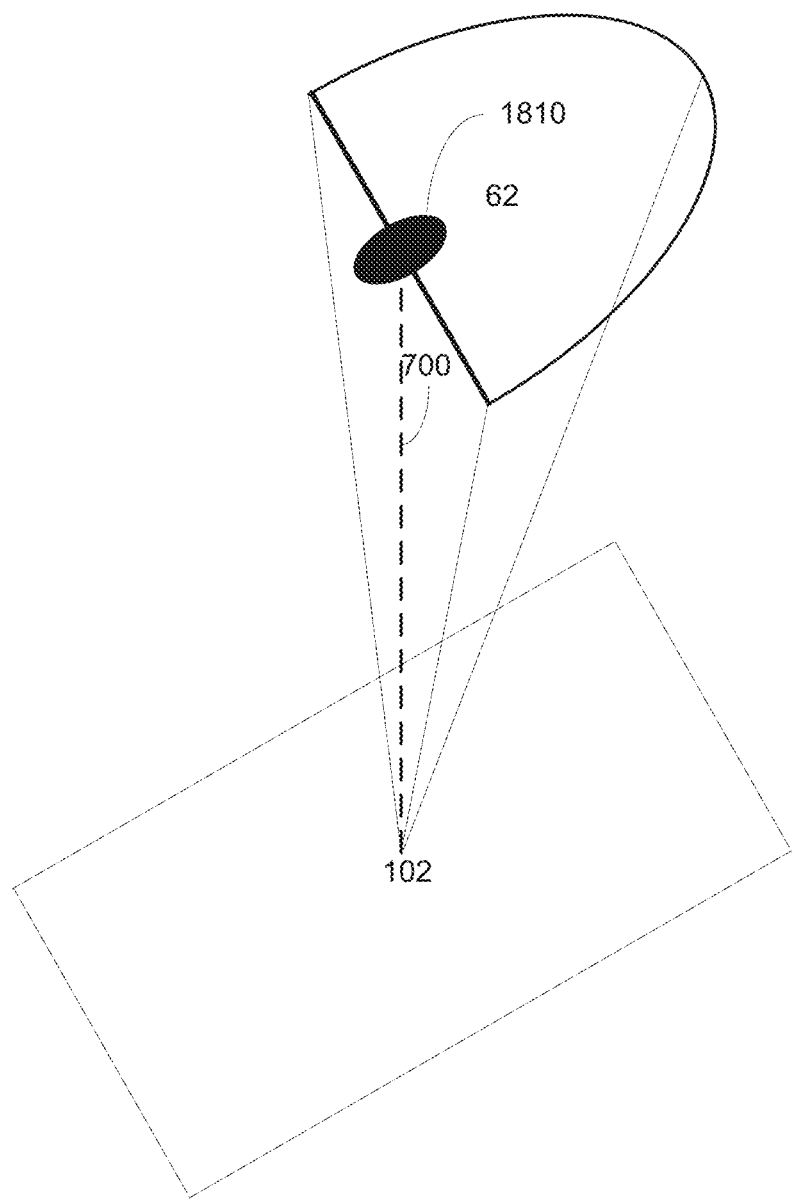

FIG. 18 illustrate a first illumination area that includes a first half cone of light and overlap area 1810 that are eventually collected by a first pupil segment 61 and FIG. 19 illustrates a second illumination area that includes a second half cone of light and overlap area 1810 of light connected by the second pupil segment 62.

Overlap area 1810 is collected by both pupils and may be used for aligning the images collected by the different detectors associated with the different pupil segments. It is noted that the overlap can be between more than a pair of pupil segments.

Referring back to FIG. 1—the image processor 90 may be arranged to process pupil segment detection signals from at least two different pupil segments to provide shape information of the surface of the sample. It may, for example, process pupil segment detection signals from at least two different pupil segments to provide amplitude and phase information relating to the surface of the sample.

According to an embodiment of the invention the image processor 90 may be arranged to sum pupil segment detection signals from at least two different pupil segments to provide the amplitude information and to subtract pupil segment detection signals from at least two different pupil segments to provide the phase information.

FIG. 17 illustrates system 1700 according to an embodiment of the invention. System 1700 has dark-field optics and differs from system 10 of FIG. 1 by having dark-field beam splitter 1740 that directs off-axis radiation scattered from object 100 towards pupil 60.

FIG. 20 illustrates system 2000 according to an embodiment of the invention. System 2000 has transmissive optics and differs from system 10 of FIG. 1 by having not having a beam splitter 40 and by positioning the pupil and the detectors to receive transmission radiation that passes through object 100. While not shown in FIG. 20, it should be noted that system 2000 with its transmissive optics can be combined with e.g. system 10 with its bright-field optics, or with any other system reflective system, e.g. off-axis systems.

FIG. 2 illustrates first and second pupil segment detection signals obtained at a presence of defects of various types.

FIG. 2 includes four graphs. The x-axis of each graph represents a position along a scan line wherein a defect is located at a position 200 along the scan line. The y-axis of each graph represents the intensity (GL gray level) of the first and second pupil segment detection signals.

Each graph includes a continuous curve (201, 203, 205 and 207) that represents the first pupil segment detection signals and a dashed curve (202, 204, 206 and 208) that represents the second pupil segment detection signals.

The upper left graph includes curves 201 and 202 that have a minimal value at location 200—where an 'absorbing' defect (absorbs more light than its surroundings) is located.

The upper right graph includes curves 203 and 204 that have a maximal value at location 200—where a 'refractive' defect (refracts more light than its surroundings) is located.

The lower left graph includes curves 205 and 206. Curve 206 is higher than curve 205 at the left side of location 200, whereas curve 206 has a positive peak to the left and in proximity to location 200 and curve 205 has a negative peak to the left and in proximity to location 200. Curve 205 is higher than curve 206 at the right side of location 200, whereas curve 205 has a positive peak to the right and in proximity to location 200 and curve 206 has a negative peak to the right and in proximity to location 200. The inspected defect is a 'positive phase shift' defect (the defect introduced a phase shift that is more positive than the phase shift introduced by its surroundings).

The lower right graph includes curves 208 and 207. Curve 207 is higher than curve 208 at the left side of location 200, whereas curve 207 has a positive peak to the left and in proximity to location 200 and curve 208 has a negative peak to the left and in proximity to location 200. Curve 208 is higher than curve 207 at the right side of location 200, whereas curve 208 has a positive peak to the right and in proximity to location 200 and curve 207 has a negative peak to the right and in proximity to location 200. The inspected defect is a 'positive phase shift' defect (the defect introduced a phase shift that is more positive than the phase shift introduced by its surroundings).

FIG. 3 provides simulation results of first and second pupil segment detection signals obtained when simulating different defects according to various embodiments of the invention.

This figure shows multiple images. The X and Y axes of the scales near each images represent X-axis and Y-axis coordinates (in microns), wherein coordinate (0,0) is the center of each image. Each image includes 128 rows of 128 pixels each. Each image also include information about a minimal and maximal normalized reflection level (wherein a value of one represents a reflection from a perfect mirror) of pixels of that image. Thus, for example and referring to image 350, "128×128, Max: 0.425, Min 0.386" indicates that the image has 128×128 pixels, that the maximum normalized reflection value is 0.425 and the minimal normalized reflection value is 0.386.

Images 310 and 320 are reconstructed from first and second pupil segment detection signals (left field, right field) assuming that a reflectivity of the defect is 20% below the reflectivity of its surroundings.

Images 330 and 340 are reconstructed from first and second pupil segment detection signals assuming that a reflectivity of the defect is 20% above the reflectivity of its surroundings.

Images 350 and 360 are reconstructed from first and second pupil segment detection signals assuming that a phase shift introduced by the defect is 30 degrees above the phase shift introduced by its surroundings.

Images 370 and 380 are reconstructed from first and second pupil segment detection signals assuming that a phase shift introduced by the defect is 30 degrees below the phase shift introduced by its surroundings.

Figure 4:
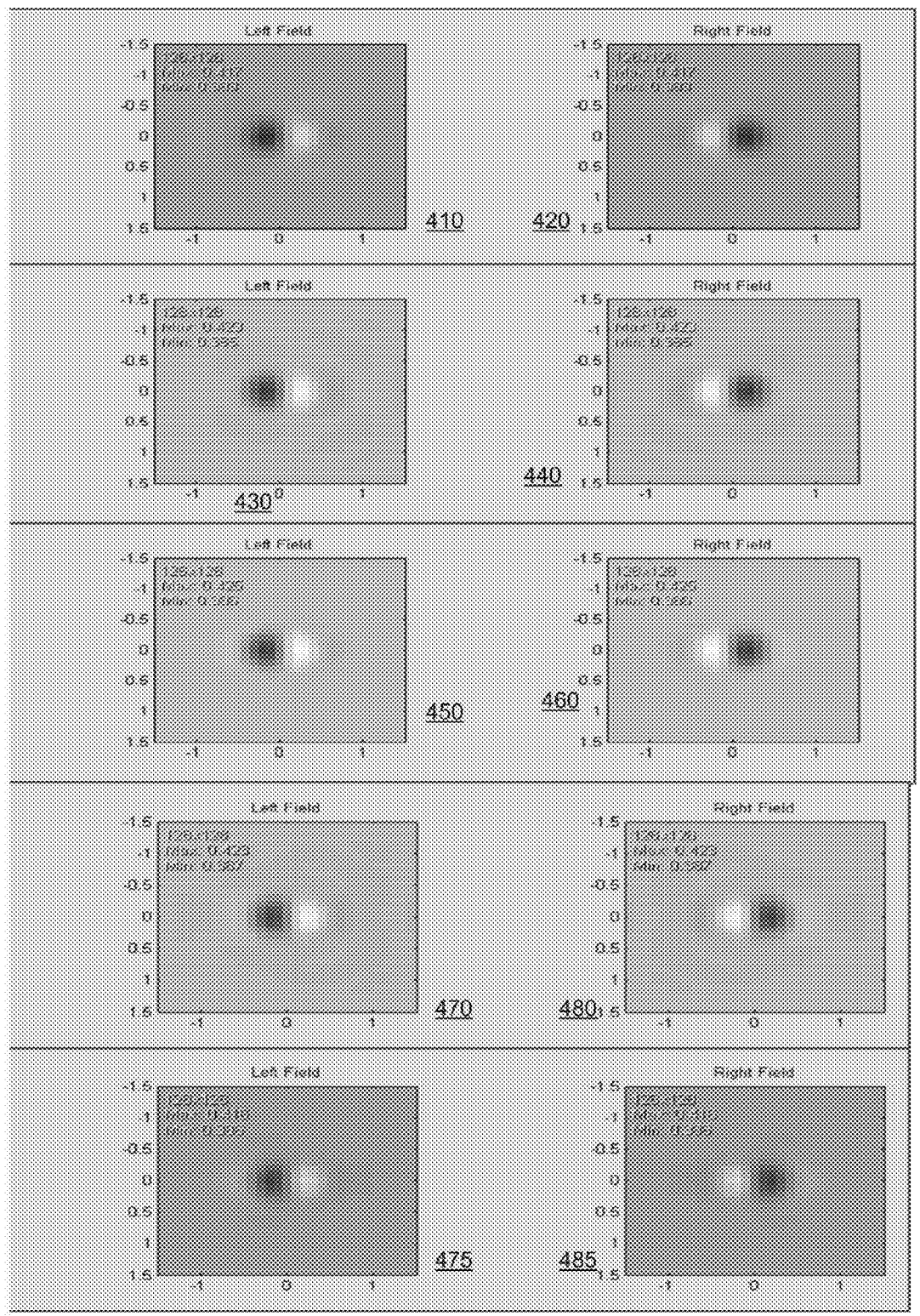
FIG. 4 illustrates simulation results of various pupil segment detections signals according to various embodiments of the invention.

FIG. 4 includes simulation results of first and second pupil segment detection signals obtained under different focus conditions according to various embodiments of the invention.

FIG. 4 illustrates that the first and second pupil segment detection signals are robust to defocus.

Images 410, 430, 450, 470 and 475 are reconstructed from first pupil segment detection signals assuming that the focus conditions are +1 DOF, +0.5 DOF, zero DOF, −0.5 DOF and −1 DOF, respectively.

Images 420, 440, 460, 480 and 485 are reconstructed from second pupil segment detection signals assuming that the focus conditions are +1 DOF, +0.5 DOF, zero DOF, −0.5 DOF and −1 DOF, respectively.

Figure 5:
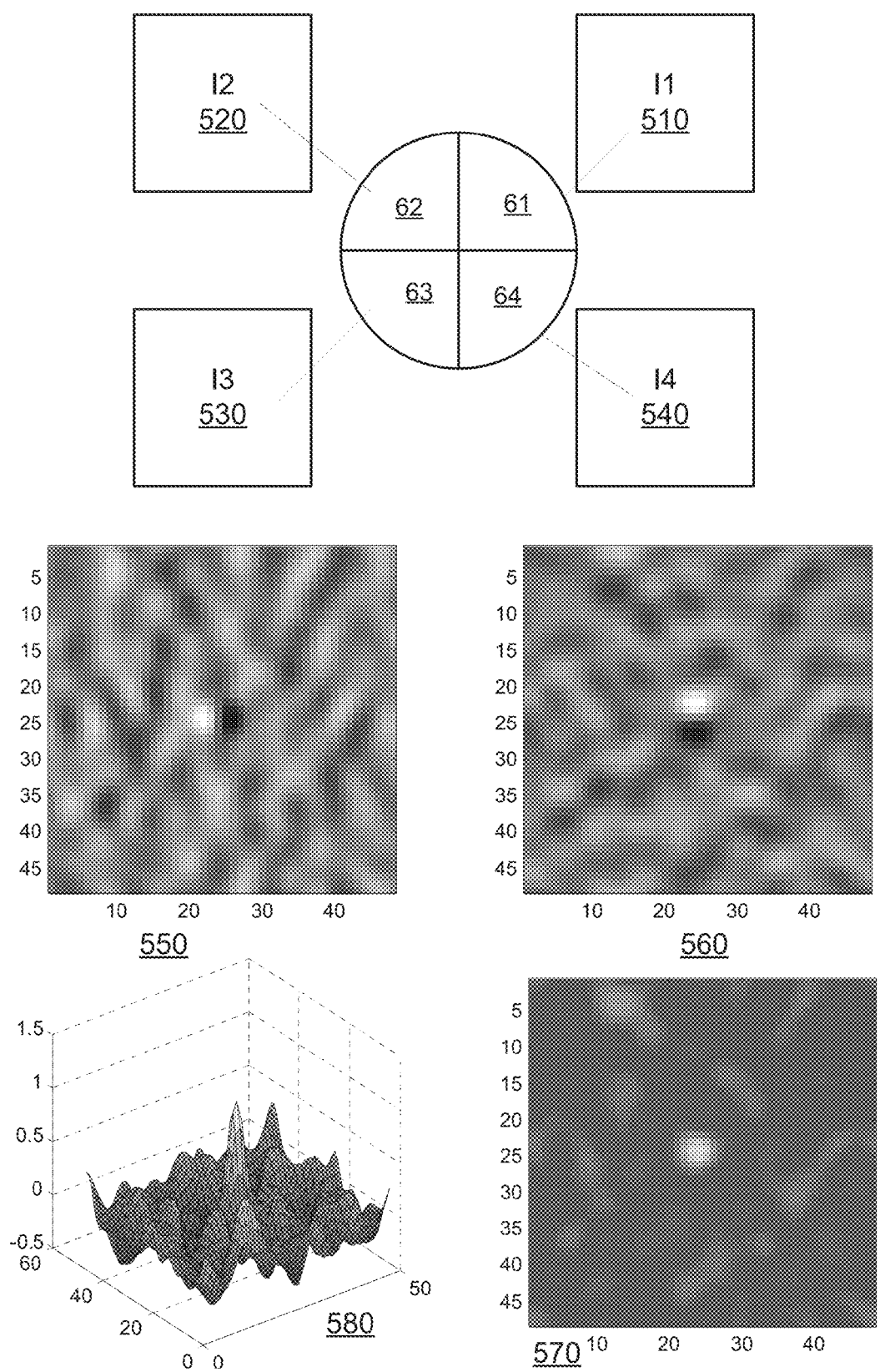
FIG. 5 illustrates a four segment pupil, multiple images and a height map according to various embodiments of the invention.

FIG. 5 illustrates a four-segment 61-64 pupil, four pupil segment images 510-540, gradient images 550 and 560, sum image 570 and a three-dimensional height map 580 according to an embodiment of the invention.

The four pupil segment images I1-I4 510-540 are reconstructed from first till fourth pupil segments 510, 520, 530 and 540 respectively.

X-axis gradient image 550 ($\partial_x$) can be calculated by: (I1+I4)−(I2+I3). This image can be normalized by the sum of all four images (I1+I2+I3+I4).

Y-axis gradient image 560 ($\partial_y$) can be calculated by: (I1+I2)−(I4+I3). This image can be normalized by the sum of all four images (I1+I2+I3+I4).

Images 550 and 560 can be combined to provide combined image 570.

The height (H) map (such as height map 580) can be calculated by methods known in the art.

It is noted that the system can apply height calculation algorithms such as those illustrates in U.S. patent application Ser. No. 13/365,238 which is incorporated herein by reference or any shape from shading algorithm such as those illustrated in "Shape from shading: a survey", Rue Zhang, Pattern analysis and machine intelligence, Volume 21, issue 8, pages 690-706, August 1999.

Figure 6:
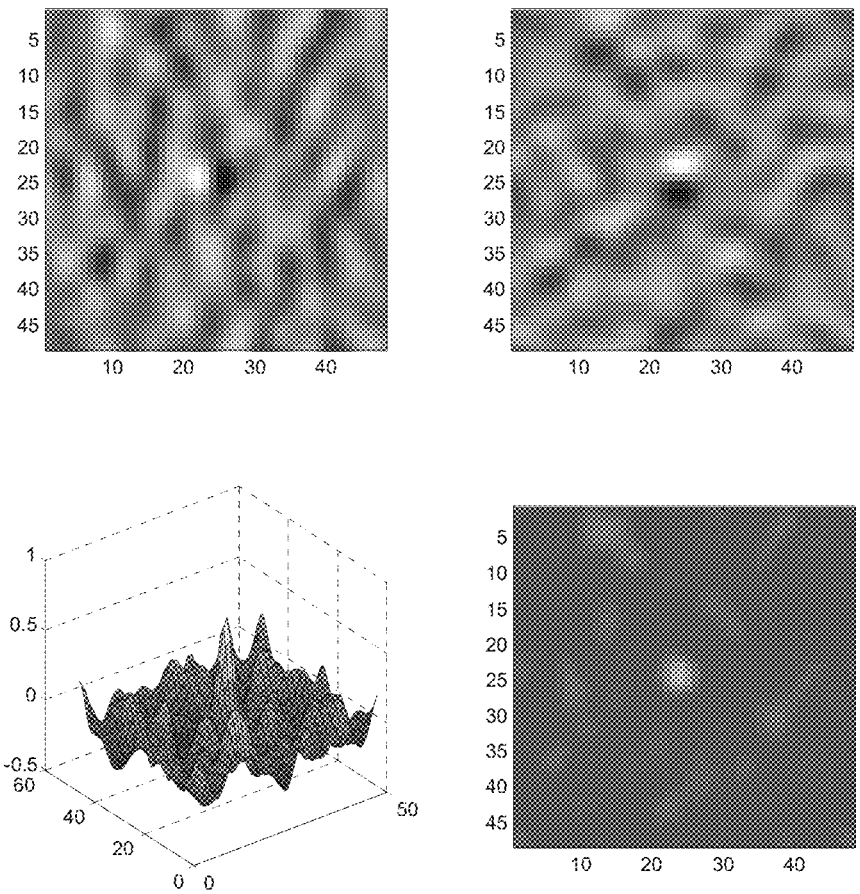
FIG. 6 illustrates multiple images obtained using a three-segment pupil and a height map according to various embodiments of the invention.

FIG. 6 illustrates an X-axis gradient image 610, a Y-axis gradient image 620, a summed image 630 and a three-dimensional height map 640 according to an embodiment of the invention.

Figure 10:
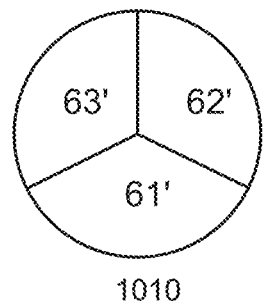
FIG. 10 illustrates various pupils according to various embodiments of the invention.
Figure 10:
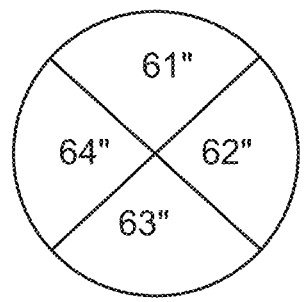

These images are obtained when using a pupil that has three pupil segments—such as pupil 1010 of FIG. 10. Pupil 1010 has evenly shaped and sized pupil segments 61'-63'. FIG. 10 also illustrates a four-segment pupil 1020 that includes pupil segments 61"-64". It should be noted that pupil 1010 and pupil 1020 can be used, with any system such as system 10 illustrated in FIG. 1, system 10' illustrated in FIG. 11, system 10" illustrated in FIGS. 12-14, system 1700 illustrated in FIG. 17, system 2000 illustrated in FIG. 20, with the appropriate modifications.

FIG. 11 illustrates an apparatus 10' and sample 100 according to an embodiment of the invention.

Apparatus 10' includes a pupil 60' with three pupil segments that is located at the illumination path. Radiation from radiation source 32 impinges on the pupil 60'. Radiation from the three pupil segments represents different illumination angular ranges 11', 12' and 13'. The radiation passes through three beam splitters 41-43 to impinge on objective lens 50 and to be directed onto sample 100. Radiation reflected from object 100 passes through objective lens 50 and is directed by beam splitters 41-43 towards detectors 71'-73' so that each detector detects light that passed via a unique pupil segment.

Detectors 71'-73' may be coupled to an image processor (not shown).

Pupil 60', beam splitters 41-43 and objective lens 50 may belong to bright-field optics of apparatus 10.

FIGS. 12-14 illustrates an apparatus 10" and sample 100 according to an embodiment of the invention.

Apparatus 10" includes a pupil 60' with three pupil segments that is located at the illumination path.

Radiation from radiation source 32 is followed by deflector 33 (or other beam path affecting element) and is arranged to illuminate one segment at a time. FIG. 12 illustrates an illumination of left upper pupil segment, FIG. 13 illustrates the illumination of bottom segment and FIG. 14 illustrates the illumination of the right upper segment.

Radiation from the three pupil segments represents different illumination angular ranges 11', 12' and 13'. At each of the three points in time (corresponding to FIGS. 12-14) the radiation passes through a single beam splitter out of beam splitters 41'-43' to impinge on objective lens 50 and to be directed onto sample 100. Radiation reflected from object 100 passes through objective lens 50 and is directed by a single beam splitter of beam splitters 41'-43' towards detector 70 so that detector 70 detects light that passed via a unique pupil segment at each of these three points in time.

Detector 70 may be coupled to an image processor (not shown).

Pupil 60', beam splitters 41'-43' and objective lens 50 may belong to bright-field optics of apparatus 10.

Figure 15:
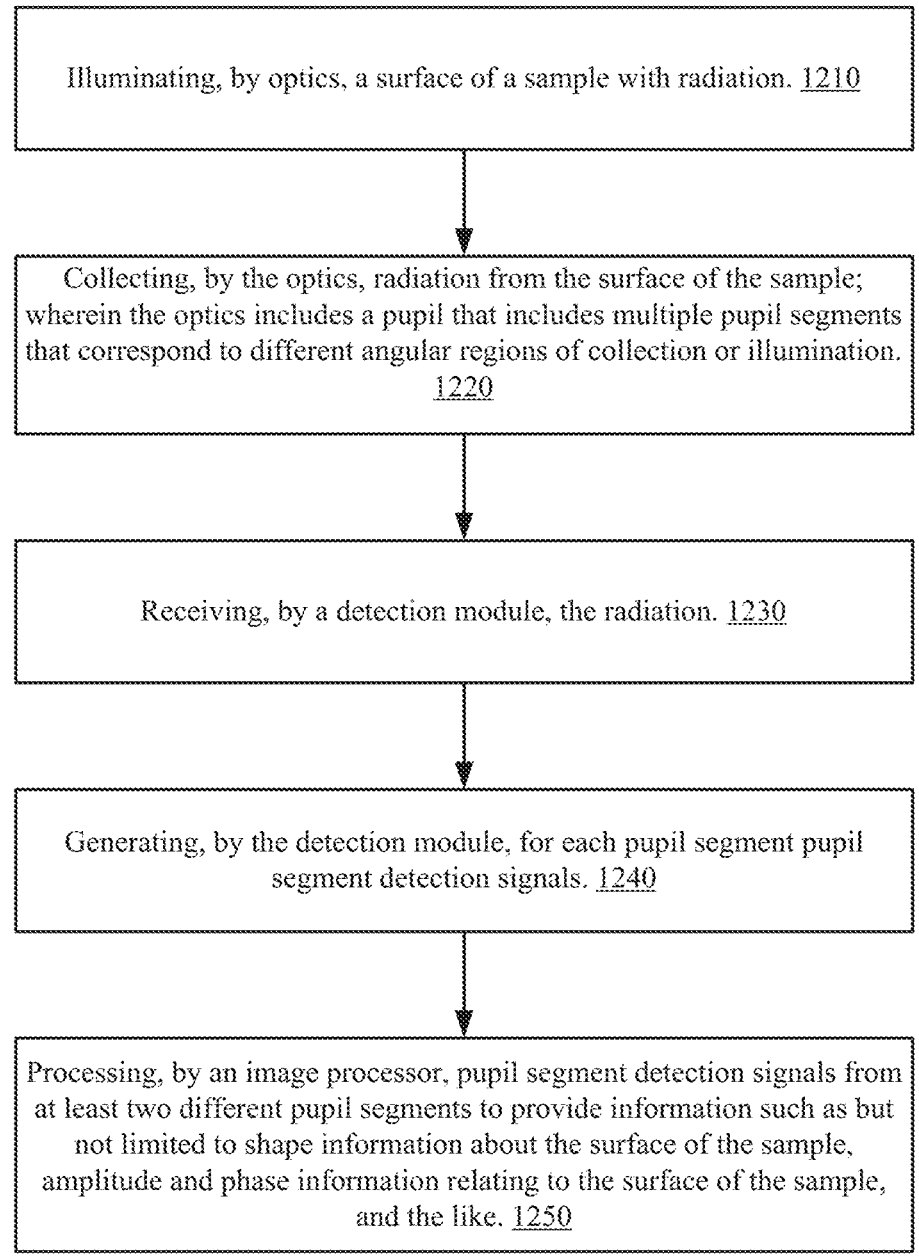
FIG. 15 illustrates a method according to an embodiment of the invention.

FIG. 15 illustrates method 1200 according to an embodiment of the invention.

Method 12 may include illuminating (1210), by optics, a surface of a sample with radiation; collecting (1220), by the optics, radiation from the surface of the sample (e.g. reflected from the surface, transmitted by the surface, or a combination thereof); wherein the optics includes a pupil that includes multiple pupil segments that correspond to different angular regions of collection or illumination; receiving (1230), by a detection module, the radiation; and generating (1240), by the detection module, for each pupil segment pupil segment detection signals.

Method 1200 may also include processing (1250), by an image processor, pupil segment detection signals from at least two different pupil segments to provide information such as but not limited to shape information about the surface of the sample, amplitude and phase information relating to the surface of the sample, and the like.

Stage 1250 may include at least one of the following: (a) summing pupil segment detection signals from at least two different pupil segments to provide the amplitude information; (b) subtracting pupil segment detection signals from at least two different pupil segments to provide the phase information; (c) calculating gradients, (d) solving Poisson equations, (e) applying shadow to height algorithms.

Figure 16:
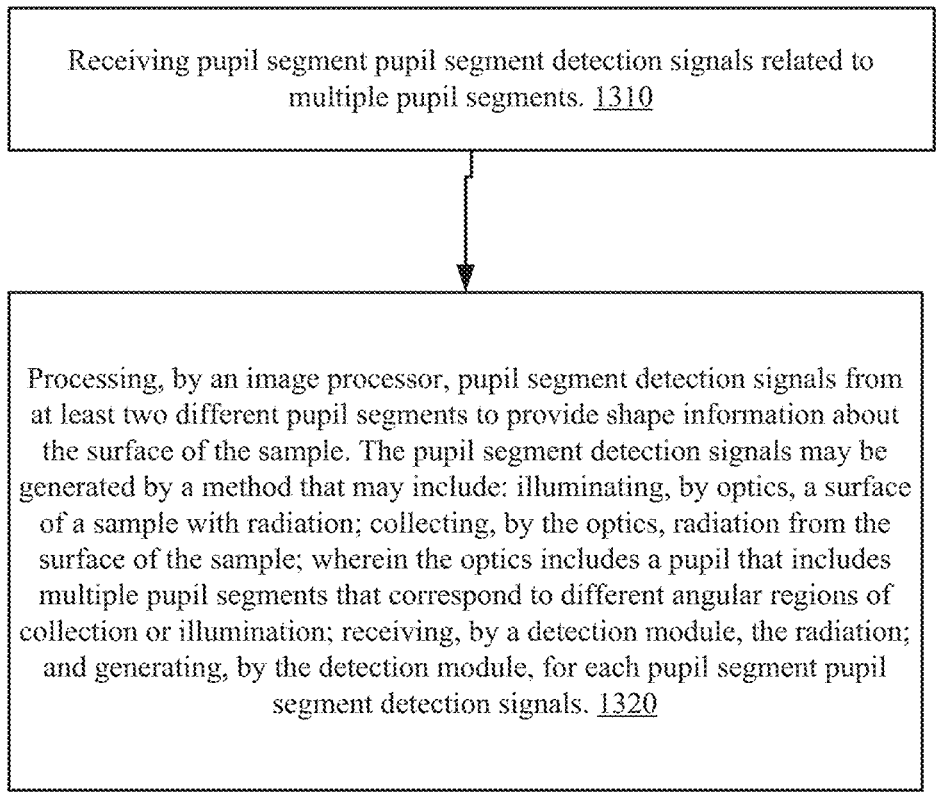
FIG. 16 illustrates a method according to an embodiment of the invention.

FIG. 16 illustrates method 1300 according to an embodiment of the invention.

Method 1300 may include receiving (1310) pupil segment pupil segment detection signals related to multiple pupil segments; and processing (1320), by an image processor, pupil segment detection signals from at least two different pupil segments to provide shape information about the surface of the sample. The pupil segment detection signals may be generated by a method that may include stages 1210-1240 of method 1200.

The invention may also be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein can be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An apparatus comprising:
   optics arranged to illuminate a surface of a sample and to collect radiation from the surface of the sample, the optics comprising:
      a pupil having multiple pupil segments that correspond to different angular regions of collection or illumination; and
      optical components configured to direct radiation from or to different pupil segments to different directions;
   a detection module arranged to receive the radiation from or to the different pupil segments and generate an image of the sample for each corresponding pupil segment; and
   an image processor arranged to:
      obtain a difference image by subtracting a first image corresponding to a first pupil segment from a second image corresponding to a second pupil segment to provide gradient of phase information associated with the surface of the sample; and
      integrate the difference image to provide a phase map of the surface of the sample.

2. The apparatus according to claim 1 wherein the image processor is further arranged to provide shape information of the surface of the sample based on the phase map of the surface of the sample.

3. The apparatus according to claim 1 wherein the image processor is further arranged to process images from at least two different pupil segments to provide amplitude information relating to the surface of the sample.

4. The apparatus according to claim 1 wherein the image processor is further arranged to sum images from at least two different pupil segments to provide amplitude information relating to the surface of the sample.

5. The apparatus according to claim 1 wherein the optics are arranged to scan the surface of the sample with a beam of radiation and wherein the multiple pupil segments correspond to different angular regions of collection.

6. The apparatus according to claim 1 wherein the optics applies area illumination and wherein the multiple pupil segments correspond to different angular regions of illumination.

7. The apparatus according to claim 1 wherein the detection module is arranged to receive the radiation from all of the pupil segments concurrently.

8. The apparatus according to claim 1 wherein the detection module is arranged to receive the radiation from a single pupil segment at a time.

9. The apparatus according to claim 1 wherein the optics is arranged to illuminate one pupil segment at a time.

10. The apparatus according to claim 1 wherein a multiplicity of pupil segments correspond to a multiplicity of different angular regions of illumination that are partially overlapping to provide an overlap region; and wherein the image processor is arranged to align images from the multiplicity of the pupil segments based on images of the overlap region.

11. The apparatus according to claim 1 wherein the optics are bright field optics.

12. A method for obtaining information about a surface of a sample, the method comprises:
   illuminating, by optics, a surface of a sample;
   collecting, by the optics, radiation from the surface of the sample wherein the optics comprises:
      a pupil that comprises multiple pupil segments that correspond to different angular regions of collection or illumination; and
      optical components configured to direct radiation from or to different pupil segments to different directions;
   receiving, by a detection module, the radiation from or to the different pupil segments;
   generating, by the detection module, an image of the sample for each corresponding pupil segment;
   obtaining, by an image processor, a difference image by subtracting a first image corresponding to a first pupil segment from a second image corresponding to a second pupil segment to provide gradient of phase information associated with the surface of the sample; and
   integrating, by the image processor, the difference image to provide a phase map of the surface of the sample.

13. The method according to claim 12 further comprising processing, by the image processor, the phase map to provide shape information about the surface of the sample.

14. The method according to claim 12 further comprising processing, by the image processor, images from at least two different pupil segments to provide amplitude information relating to the surface of the sample.

15. The method according to claim 12 further comprising: summing images from at least two different pupil segments to provide the amplitude information.

16. The method according to claim 12 wherein a pair of pupil segments correspond to a pair of different angular regions of illumination that are partially overlapping to provide an overlap region; and the method further comprises aligning images from the pair of the pupil segments based on images of the overlap region.

17. A non-transitory computer-readable medium that stores instructions that cause a computer to:
  receive pupil segment images of a sample, each pupil segment image related to one of multiple pupil segments; and
  process pupil segment images from at least two different pupil segments to provide shape information about a surface of the sample;
  wherein the pupil segment images are generated by:
    illuminating, by optics, a surface of a sample;
    collecting, by the optics, radiation from the surface of the sample; wherein the optics comprises an pupil having the multiple pupil segments; wherein different pupil segments correspond to different angular regions of collection or illumination; and wherein the optics further comprises optical components configured to direct radiation from or to the different pupil segments to different directions;
    receiving, by a detection module, the radiation from or to the different pupil segments; and
    generating, by the detection module, a pupil segment image of the sample for each pupil segment; and
  wherein processing pupil segment images from at least two different pupil segments to provide shape information about the surface of the sample includes:
    obtaining a difference image by subtracting a first pupil segment image corresponding to a first pupil segment from a second pupil segment image corresponding to a second pupil segment to provide gradient of phase information associated with the surface of the sample; and
    integrating the difference image to provide a phase map of the surface of the sample.

18. The non-transitory computer readable medium according to claim 17 that stores instructions that cause the computer to process pupil segment images from at least two different pupil segments to provide amplitude information relating to the surface of the sample.

19. The non-transitory computer readable medium according to claim 17 that stores instructions that cause the computer to sum pupil segment images from at least two different pupil segments to provide the amplitude information of the surface of the sample.

20. The apparatus according to claim 1 wherein the optical components include a plurality of beam splitters, each beam splitter arranged to direct radiation from or to a different pupil segment to a different direction.

21. The apparatus according to claim 1 wherein the optical components include a plurality of diffraction gratings, each diffraction grating arranged to direct radiation from or to a different pupil segment to a different direction.

22. The apparatus according to claim 1 wherein the optics are dark field optics or gray field optics.

\* \* \* \* \*